US005798242A

United States Patent [19]
Fujishiro et al.

[11] Patent Number: 5,798,242
[45] Date of Patent: *Aug. 25, 1998

[54] CHOLESTEROL OXIDASE

[75] Inventors: Kinya Fujishiro, Shizuoka-ken; Takayuki Uwajima, Machida, both of Japan

[73] Assignee: Kyowa Hakko Kogyo Co., Ltd., Tokyo, Japan

[*] Notice: The term of this patent shall not extend beyond the expiration date of Pat. No. 5,371,005.

[21] Appl. No.: 759,579

[22] Filed: Dec. 5, 1996

Related U.S. Application Data

[62] Division of Ser. No. 460,114, Jun. 2, 1995, Pat. No. 5,665,560, which is a division of Ser. No. 262,338, Jun. 17, 1994, Pat. No. 5,602,017, which is a continuation of Ser. No. 14,531, Feb. 8, 1993, Pat. No. 5,371,005, which is a continuation of Ser. No. 798,660, Nov. 26, 1991, abandoned, which is a continuation-in-part of Ser. No. 683,539, Apr. 10, 1991, abandoned.

[30] Foreign Application Priority Data

Apr. 10, 1990 [JP] Japan ................................ 2-94296

[51] Int. Cl.$^6$ ........................................................ C12N 9/04
[52] U.S. Cl. .................................................. 435/190; 435/11
[58] Field of Search ............................................... 435/190

[56] References Cited

U.S. PATENT DOCUMENTS 5,371,005  12/1994  Fujishiro et al. ....................... 435/190

FOREIGN PATENT DOCUMENTS

90/05788  5/1990  WIPO .
94/25603  11/1994  WIPO .

OTHER PUBLICATIONS

Liu et al., Agric. Biol. Chem. 52:413–418, 1988.

*Primary Examiner*—Eric Grimes
*Attorney, Agent, or Firm*—Antonelli, Terry, Stout & Kraus, LLP

[57] ABSTRACT

A cholesterol oxidase having a particular amino acid sequence and having a high substrate affinity and a working pH in an acidic range is produced by *Brevibacterium sterolicum*.

2 Claims, 8 Drawing Sheets

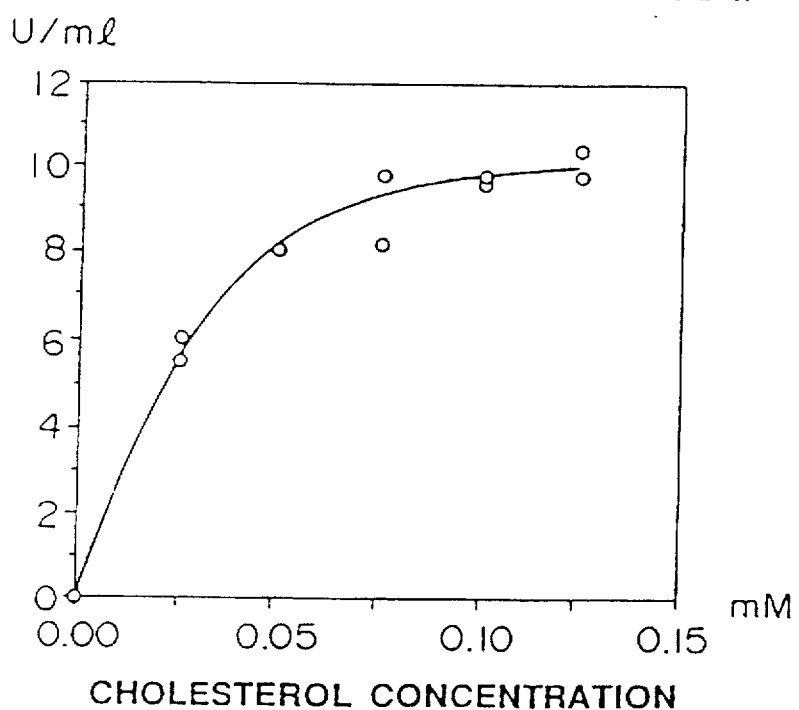
FIG. 5A CHOLESTEROL OXIDASE II
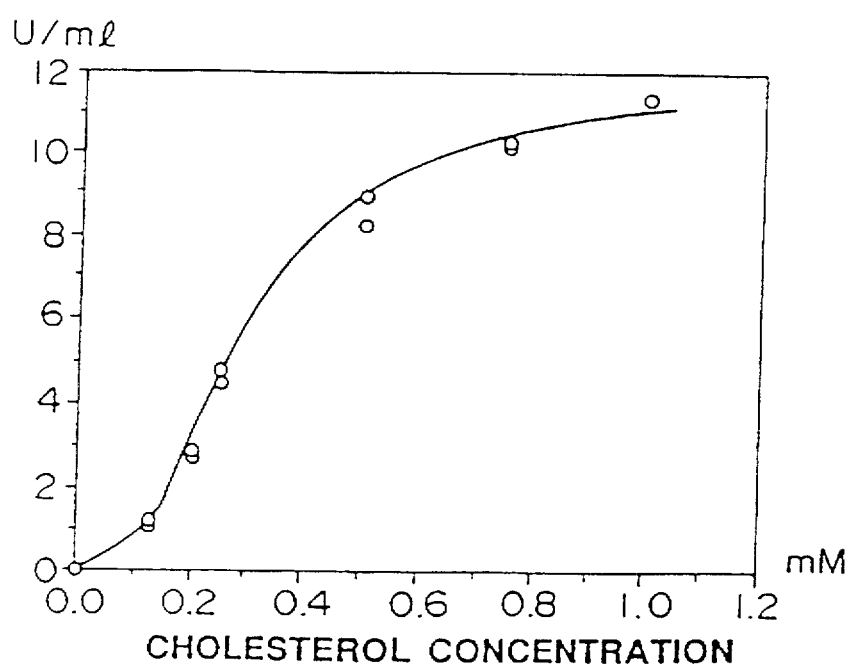
FIG. 5B CHOLESTEROL OXIDASE I FRACTION NUMBER (10ml/TUBE)

CHOLESTEROL OXIDASE

This application is a Divisional application of prior application Ser. No. 08/460,114, filed Jun. 2, 1995, (now U.S. Pat. No. 5,665,560) which is a Divisional application of prior application Ser. No. 08/262,338, filed Jun. 17, 1994, (now U.S. Pat. No. 5,602,017) which is a Continuation of application Ser. No. 08/014,531, filed Feb. 8, 1993, (now U.S. Pat. No. 5,371,005) which is a Continuation application of Ser. No. 07/798,660, filed Nov. 26, 1991, (now abandoned) which is a Continuation-in-Part of Ser. No. 07/683,539, filed Apr. 10, 1991 (now abandoned).

BACKGROUND OF THE INVENTION

The present invention relates to a novel cholesterol oxidase having a high substrate affinity and the working pH in an acidic range.

Cholesterol oxidase is an enzyme which catalyzes the reaction of oxidizing cholesterol (5-cholesten-3-β-ol) as substrate into 4-cholesten-3-one and hydrogen peroxide. The enzyme is used in a clinical test for quantitative determination of cholesterol in blood, etc.

It is known that cholesterol oxidase has been produced by a microorganism belonging to the genus Schizophyrum, Streptoverticillium, Brevibacterium or Streptomyces in an industrial scale. However, it has been pointed out that a known cholesterol oxidase used for quantitative determination of cholesterol in blood has a low substrate affinity. Hence, there is a problem in quantitative determination accuracy where a sample solution having a low cholesterol content is analyzed and where a diluted sample solution is assayed. It has been further pointed out that the working pH range for the activity of known enzymes is relatively narrow so that when pH of a sample is set in an acidic range, for example at around 6, in order to avoid an influence by other components such as bilirubin, the enzyme activity is lowered. In addition, productivity of the aforementioned cholesterol oxidase-producing microorganisms is extremely low and multiple procedures for purification of enzymes are requried to remove protein impurities.

Therefore, it has been desired to develop a cholesterol oxidase having a high substrate affinity and a wide working pH range as well as a microorganism capable of producing cholesterol oxidase in high productivity without contamination with protein impurities.

As a result of extensive studies in cholestrol oxidases, it has now been found that a novel cholesterol oxidase having a high substrate affinity and a wide working pH in an acidic range can be produced in good yield, by culturing a microorganism which is constructed by the steps of: isolating, from a strain belonging to the genus Brevibacterium, a DNA fragment bearing genetic information involved in the production of a different isoenzyme in the substrate affinity, working pH range and isoelectric point from known cholesterol oxidase, inserting the DNA fragment into a vector DNA to prepare a recombinant DNA containing the DNA fragment, introducing the recombinant DNA into a microorganism belonging to the genus Escherichia. The present invention has thus been accomplished.

SUMMARY OF THE INVENTION

The present invention provides a novel cholesterol oxidase (hereafter referred to as cholesterol oxidase II) which has nucleotide sequence as defined in the Sequence Listing by SEQ ID: No. 1 and the following physicochemical properties, a process for production of cholesterol oxidase II, and a method for quantitative determination of cholesterol in a sample.

(a) Activity

It catalyzes the reaction of oxidizing cholesterol in the presence of oxygen to form hydrogen peroxide and 4-cholesten-3-one.

(b) Isoelectric point: pH 4.7

(c) Substrate Specificity

It acts on cholesterol, β-sitosterol, stigmasterol, pregnenolone, dehydroisoandrosterone and estradiol but does not act on vitamin $D_3$, cholic acid, androsterone, cholesterol linoleate or lanosterol.

(d) Working pH Range and Stable pH Range

The working pH is in a range of 5.0 to 7.5. The enzyme is stable in a pH range of 5.3 to 7.5, when heated at 50° C. for 60 minutes.

(e) Optimum temperature: about 50° C.

(f) Conditions for Inactivation by pH and Temperature

The enzyme is inactivated at a pH of 10.0 or more or at a pH of 4.0 or less when heated at 50° C. for an hour. The enzyme is also inactivated by about 83% when heated at a pH of 7.0 and a temperature of 60° C. for an hour.

(g) Inhibition and Stabilization

The enzyme is inhibited by p-chloromercury benzenesulfonate, silver nitrate and o-hydroxyquinoline. Further in the presence of bovine serum albumin, resistance to heat and stability during storage are improved.

(h) Michaelis' constant to cholesterol (Km value): $3.0 \times 10^{-5}$M (i) Molecular Weight about 43,000 (gel filtration)

about 60,000 (electrophoresis)

66,586 (DNA sequence)

BRIEF DESCRIPTION OF THE DRAWINGS

FIGS. 5A and 5B show substrate saturation curve of cholesterol oxidases I and II on the purified cholesterol. FIG. 5 (A) and FIG. 5 (B) denote the results obtained by use of cholesterol oxidase II and cholesterol oxidase I, respectively.

DETAILED DESCRIPTION OF THE INVENTION

Figure 1:
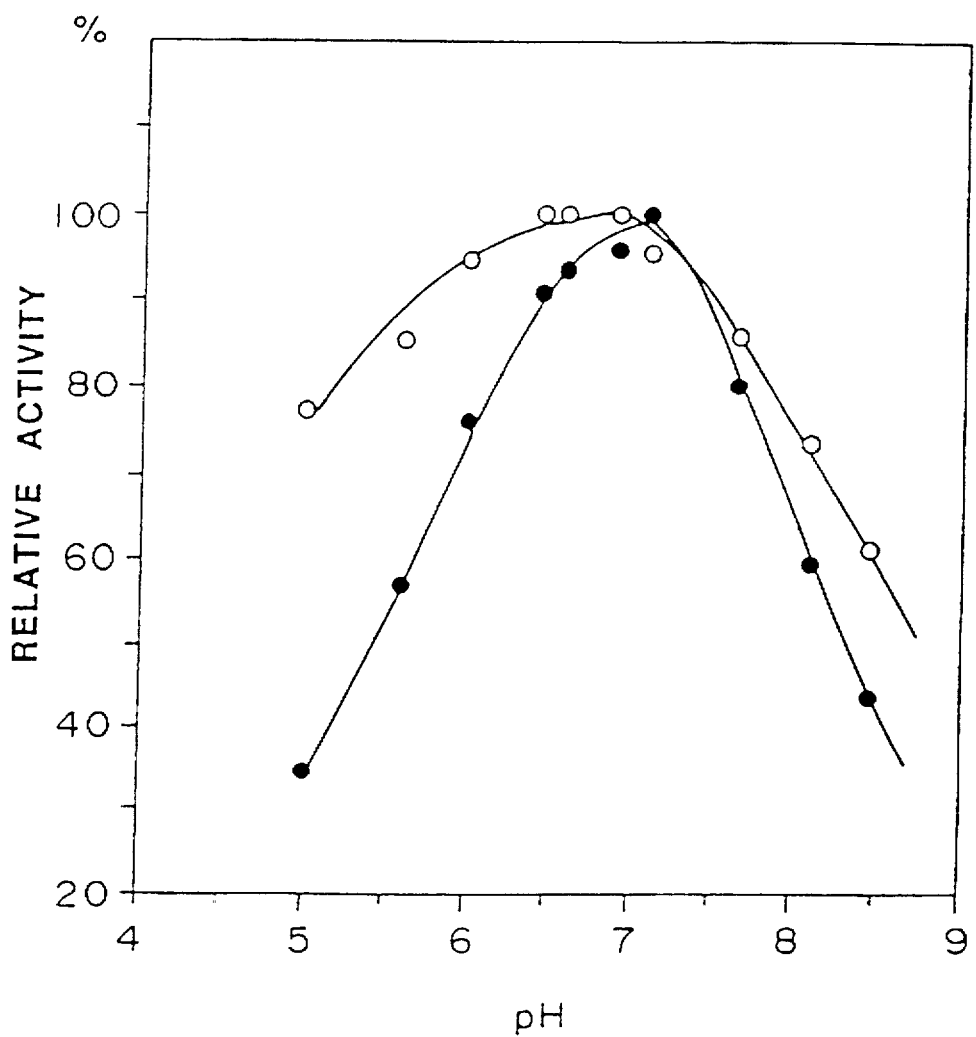
FIG. 1 shows relative activities of cholesterol oxidases I and II at respective pH values after treated at 37° C. for 5 minutes. In the figure, ○ denotes the activity of cholesterol oxidase II and ● denotes the activity of cholesterol oxidase I.

Cholesterol oxidase II is an enzyme newly isolated from *Brevibacterium sterolicum* ATCC 21387 described in Japanese Published Examined Patent Application No. 1190/73. The strain has been known to be a cholesterol oxidase-producing strain. Cholesterol oxidase II is a novel enzyme having properties different from those of a known cholesterol oxidase (hereafter referred to as cholesterol oxidase I) derived from ATCC 21387 strain. Comparison between Cholesterol oxidases II and I are given below.

(1) Isoelectric Point

Cholesterol oxidase II has an isoelectric point of pH 4.7, whereas an isoelectric point of cholesterol oxidase I is pH 8.9.

(2) Substrate Specificity

Substrate specificity of cholesterol oxidases I and II is shown in Table 1.

TABLE 1

| Substrate | Relative Activity (%) | |
|---|---|---|
| | I | II |
| Cholesterol | 100 | 100 |
| Dehydroisoandrosterone | 41.4 | 13.0 |
| Pregnenolone | 22.4 | 32.9 |
| β-Sitosterol | 19.7 | 82.0 |
| Stigmasterol | 10.0 | 64.4 |
| Estradiol | 0 | 3.2 |
| Vitamin $D_3$ | 0 | 0 |
| Cholic acid | 0 | 0 |
| Androsterone | 0 | 0 |
| Cholesterol linoleate | 0 | 0 |
| Lanosterol | 0 | 0 |

(3) Working pH for Activity

The working pH of cholesterol oxidase II is in a range of 5.0 to 7.5, whereas that of cholesterol oxidase I is in a range of 6.0 to 7.5.

(4) Michaelis' Constant to Cholesterol (Km Value)

The constant of cholesterol oxidase II is $3.0\times10^{-5}$M, whereas the constant of cholesterol oxidase I is $1.1\times10^{-3}$M.

(5) Influence of Inhibitor

Relative activity is shown in Table 2, in the presence of an inhibitor at a concentration of 1 mM, when in the absence of the inhibitor, the activities of cholesterol oxidases I and II are regarded as 100.

TABLE 2

| Inhibitor | Relative Activity (%) | |
|---|---|---|
| | II | I |
| p-Chloromercury benzenesulfonate | 87.0 | 80.0 |
| $AgNO_3$ | 1.0 | 0 |
| o-Hydroxyquinoline | 91.3 | — |

(6) Molecular Weight

From the analysis using TSK G3000SW manufactured by Toyo Soda Mfg. Co., Ltd., it is presumed that the molecular weight is 43,000 based on its elution pattern (gel filtration). From the analysis using SDS-PAGE, it is presumed that the molecular weight is 60,000 based on its mobility. The DNA sequence determination indicates that the molecular weight is 66,586. In the case of cholesterol oxidase I, the molecular weight is presumed to be 33,000 by analysis using Sephadex gel filtration carrier manufactured by Pharmacia Fine Chemicals, Inc., and is presumed to be 55,000 by analysis using SDS-PAGE.

Cholesterol oxidase II can be produced by culturing a microorganism having an ability to produce cholesterol oxidase II, and belonging to the genus Brevibacterium sterolicum. However, since an accumulated amount of cholesterol oxidase II is very small, it is difficult to isolate and purify the enzyme from a culture obtained by culturing a strain of Brevibacterium sterolicum in an ordinary way. By isolating chromosomal DNA from a microorganism belonging to the genus Brevibacterium sterolicum, shotgun-cloning a gene coding for cholesterol oxidase II in an appropriate host-vector system, and introducing a vector DNA containing the gene into a suitable Escherichia coli strain cholesterol oxidase II-producing strain having a high expression activity can be constructed.

Hereafter construction of the cholesterol oxidase II-producing strain is described.

Shotgun-cloning of cholesterol oxidase II encoding gene isolated from a microorganism belonging to the species Brevibacterium sterolicum can be recognized by directly determining the expressed enzyme activity using Escherichia coli as a host. The direct determination of the expressed enzyme activity can be made, for example, by using cells of a transformant as direct enzyme source, or by the method which comprises lyzing cells with lysozyme etc. and determining the enzyme activity using the resulting permeable cell, or by the method which comprises incorporating cholesterol in a medium and observing the clear halo formation associated with oxidation of cholesterol by the enzyme activity leaked out of the cells in a trace amount.

Chromosomal DNA containing the gene coding for cholesterol oxidase II is isolated from a microorganism belonging to the species Brevibacterium sterolicum in a conventional manner, for example, by the method described in Manual of Molecular Biology Experiment (R. F. Schleif, P. C. Wensink, translated by Masaya Kawakami and Tatsumi Yamasaki, published by Kodansha Scientific, 1983).

Then, the chromosomal DNA obtained above is digested with appropriate restriction enzymes to prepare a DNA fragment containing cholesterol oxidase II encoding gene. The DNA fragment may be incorporated in a conventional manner into a vector DNA digested with appropriate restriction enzymes, by use of DNA ligase to prepare the recombinant DNA containing the cholesterol oxidase II encoding gene. As the vector DNA used herein, any plasmid can be used so long as it is autonomously replicable in Escherichia coli. Inter alia, pUC13, pPROK-C, etc. are preferably used. As examples of the restriction enzyme, BamHI, Sau3AI, etc. can be used. The cleavage site of Sau3AI causes the extrusive end having the same structure as the cleavage site with BamHI so that ligation for recombination is possible. Thus, the DNA fragment obtained by subjecting chromosomal DNA to restriction digestion with Sau3AI can be ligated with the vector DNA digested with BamHI. As DNA ligase, T4 DNA ligase derived from T4 phage-infected Escherichia coli can be advantageously used.

Then, the recombinant DNA obtained by the method described above is introduced into Escherichia coli in a conventional manner, for example, by the method described in Molecular Cloning (T. Maniatis, E. F. Fritsch, J. Sambrook, Cold Spring Harbour Publishing Co., 1982). Selection of a transformant carrying the recombinant DNA containing cholesterol oxidase II-encoding gene is made as follows. That is, transformants are cultured in an LB solid medium containing 0.1% cholesterol, 0.1% Triton X-100 and 0.0025% ampicillin. Colonies around which a clear halo formation is formed are selected from the growing colonies. Then, the colonies are inoculated on a microtiter plate to assay the presence of cholesterol oxidase activity. An example of the thus obtained recombinant plasmids is pnH10. The transformant carrying the resulting plasmid pnH10, namely, *Escherichia coli* nH10, has been deposited under Budapest Treaty with the Fermentation Research Institute of the Agency, Industrial Science Technology of Japan as *Escherichia coli* nH10 (FERM BP-2850) since Apr. 5, 1990.

The thus obtained cholesterol oxidase II-producing strain is cultured in a nutrient medium, whereby marked quantities of cholesterol oxidase II are accumulated in the culture.

As the media for culturing the cholesterol oxidase II-producing strain, any of synthetic media and natural media containing carbon sources, nitrogen sources, inorganic compounds, etc. can be used. As the carbon source, there are used various carbohydrates such as lactic acid, glycerol and molasses. The preferred amount of the carbon sources used is approximately 5 to 70 g/l. As the nitrogen source, there are used ammonium sulfate, ammonium phosphate, ammonium carbonate, ammonium acetate, or nitrogen-containing organic compounds such as peptone, yeast extract, corn steep liquor, casein hydrolyzate and meat exract. The amount of the nitrogen source is preferably about 5 to 20 g/l. As the inorganic compounds, there are used, for example, sodium chloride, potassium dihydrogenphosphate, dipotassium hydrogen phosphate, magnesium sulfate, magnesium choloride, etc. The preferred amount of the inorganic compounds used is approximately 0.05 to 5 g/l. Culturing is carried out under aerobic conditions such as shaking culture and agitation submerged culture. For the culturing, it is preferred to maintain a temperature of 30 to 37° C. In general, a period for the culturing is about 16 to 40 hours.

For collecting cholesterol oxidase II from the culture after completion of the culturing, the cells are collected from the culture described above by means of centrifugation, etc. The obtained cells are homogenized by sonication, trituration using glass beads, grinding treatment with French press, etc. to extract the enzyme. The extract is treated in a conventional manner such as salting out with ammonium sulfate, chromatography using ion exchange resin, gel filtration and chromatography using hydroxyappatite adsorption resin to obtain purified cholesterol oxidase II. Cholesterol oxidase II accumulated outside the cells may be treated in the same manner as described above except for omitting the operation for cell homogenization.

The physicochemical properties of the thus obtained cholesterol oxidase II are described in detail below. With respect to Cholesterol oxidase II, the purified enzyme preparation obtained in Example 2 was used.

I. Activity

It catalyzes the reaction of oxidizing cholesterol in the presence of oxygen to form hydrogen peroxide and 4-cholesten-3-one.

(a) Ascertainment of the Formation of Hydrogen Peroxide

Cholesterol is oxidized on cholesterol oxidase II in the presence of oxygen and then peroxidase, phenol and 4-aminoantipyrine are added to the enzyme system, whereby a quinonimine pigment is formed in the reaction system.

Reaction Composition 3 mM cholesterol, 1.0% Triton X-100 aqueous solution 1.0 ml 50 mM sodium cholate aqueous solution 0.3 ml 0.5M Na-K phosphate buffer (pH 6.0) 0.3 ml 42 mM phenol aqueous solution 0.5 ml 2.4 mM 4-aminoantipyrine aqueous solution 0.5 ml 2 mg/ml peroxidase (manufactured by Toyobo Ltd., specific activity 115 units per 1 mg of protein) 0.2 ml cholesterol oxidase II aqueous solution (0.5 unit) 0.2 ml The reagents given in Reaction composition above were mixed with each other. While stirring the mixture at 37° C., the amount of produced hydrogen peroxide was determined by colorimetric determination of produced quinonimine pigment. That is, when hydrogen peroxide produced in the reaction system was determined by the method as described in Clinical Chemistry, 20, 470 (1974), it was recognized that 0.191 mole of hydrogen peroxide was formed from 0.15 μmole of cholesterol.

(b) Ascertainment of Oxygen Consumption

In the presence of oxygen, cholesterol oxidase II acts on cholesterol and an amount of oxygen consumed is measured by Warburg's manometer.

Reaction Composition 3 mM cholesterol, 1.5% Triton X-100 aqueous solution 1.0 ml 50 mM sodium cholate aqueous solution 0.3 ml 0.5M Na-K phosphate buffer (pH 6.0) 0.3 ml 42 mM phenol aqueous solution 0.5 ml 2.4 mM 4-aminoantipyrine aqueous solution 0.5 ml 2 mg/ml peroxidase (manufactured by Toyobo Ltd., specific activity 115 units per 1 mg/of protein) 0.2 ml cholesterol oxidase II aqueous solution (0.5 unit) 0.2 ml The reagents given in the reaction composition above were mixed with each other. While stirring the mixture at 37° C., a difference in gaseous pressure between the inside and outside of a reactor caused by consumption of oxygen was compensated for by shift of the manometer in a cylinder connected with the reactor at one end and connected with the outer air at another end. In this case, an amount of the manometer liquid shifted was determined. An amount of the manometer liquid shifted was converted into an amount of ideal gas in the standard state by the following equation (Umbreit Burris Stauffer, Manometric and Biochemical Techniques, 5th edition, Chapter 5).

$$V = \frac{273 \times (P - Pw) \times \Delta Vg}{760 \times T}$$

wherein symbols denote the following.

V: amount of ideal gas consumed in the standard state (unit: μl)

P: atmospheric pressure when measured (unit: mmHg)

Pw: vapor pressure at a reaction temperature when measured (unit: mmHg)

T: reaction temperature when measured (unit: K°)

ΔVg: amount of manometer liquid shifted (unit: μl)

In the standard state, 1 μl of gas corresponds to 0.0446 μmole.

The results of measurement indicates that when 1.5 μmole of cholesterol was oxidized on cholesterol oxidase II, 1.43 μmole of oxygen was consumed.

(c) Ascertainment of the Formation of 4-cholesten-3-one

In the presence of oxygen, cholesterol oxidase II acted on cholesterol, and the reaction product was identified to be 4-cholesten-3-one as follows.

Procedures for Identification

1) Reaction Solution 50 mM cholesterol ethanol solution 6.0 ml 50 mM sodium cholate aqueous solution 5.0 ml Triton X-100 1.5 ml 0.5M Na-K phosphate buffer (pH 7.5) 5.0 ml
cholesterol oxidase II aqueous solution (19 units) 13.0 ml
Water 19.5 ml 2) Reaction Procedures The reaction solution described above was subjected to reaction at 37° C. while shaking. Thirty minutes, 3 hours and 16 hours after, 50 μl each of the reaction solution was collected and mixed with 50 μl of hexane. Thereafter 5 μl of the resultant supernatant of the mixture was collected and provided for the subsequent procedure (3) for identification.

3) Identification

As the result of thin layer chromatography (hereafter referred to as TLC) shown below, the product in the reaction solution was identified to be 4-cholesten-3-one.

The thin layer plate used was silica gel G-60F-254 (trademark, manufactured by E. Merck A.G.) and a developing solvent is the solvent system [hexane:ethyl acetate= 3:2 (volume ratio)]. After development, the plate was observed in terms of fluorescent emission under exposure to UV rays (wavelength of 254 nm) followed by phosphorus molybdenate reaction. It was thus recognized that Rf value of the reaction product coincides with that of the authentic compound. The results are shown in Table 3.

TABLE 3

Identification of the Reaction Product by TLC

| Color Development | Sample | Rf value |
| --- | --- | --- |
| Exposure to UV ray (wavelength 254 nm) | Authentic 4-cholesten-3-one | 0.808 |
|  | Reaction product | 0.808 |
| Phosphorus molybdenate reagent | Authentic 4-cholesten-3-one | 0.808 |
|  | Reaction product | 0.808 |

(Note) phosphorus molybdenate reagent: Organic compounds containing carbons react with the reagent to give a black spot.

(d) Based on the amount of hydrogen peroxide formed, the amount of oxygen consumed and identification of the reaction product as described in (a), (b) and (c), it is recognized that the enzyme of the present invention acts on specifically cholesterol, that cholesterol was oxidized into hydrogen peroxide and 4-cholesten-3-one; that is, this enzyme has a cholesterol oxidase activity.

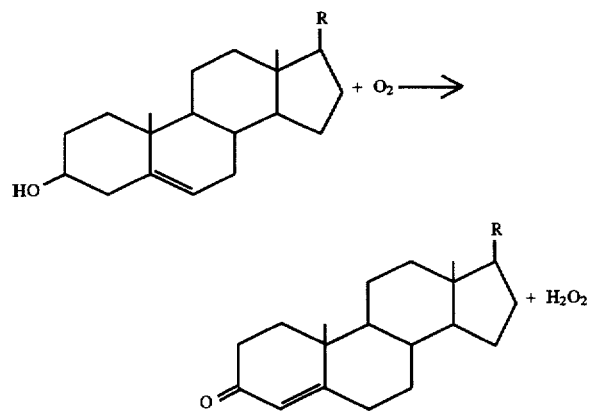

wherein R represents

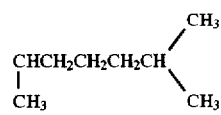

II. Working pH Range and Stable pH Range

Figure 2:
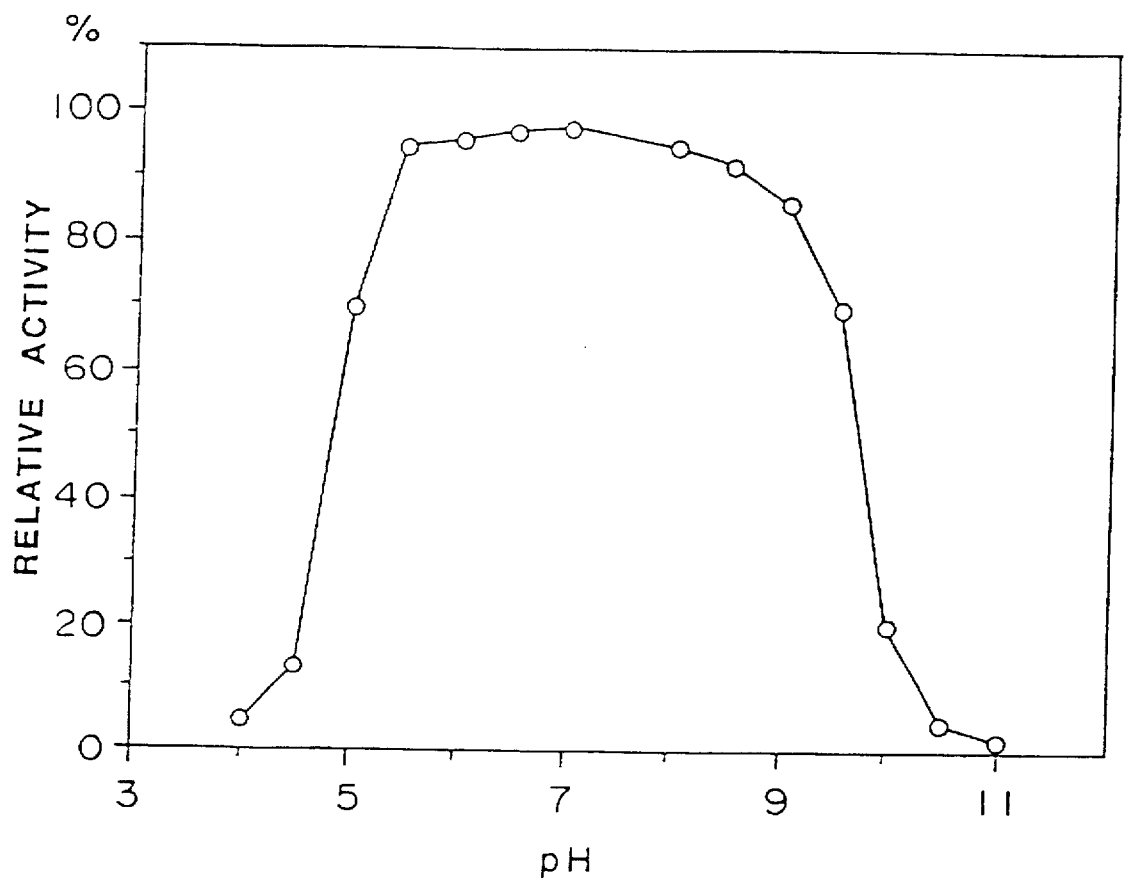
FIG. 2 shows pH stability of the purified preparation of cholesterol oxidase II.

The working pH for the activity is in a range of 5.0 to 7.5. The working pH range was determined by assaying the activity at each pH (phosphate buffer, Tris-HCl buffer, sodium acetate buffer) after the reaction at 37° C. for 5 minutes. In this case, pH ranges were also determined with respect to cholesterol oxidase I. The results are shown in FIG. 1. As shown in FIG. 1, the working pH range of cholesterol oxidase II was obviously different from that of cholesterol oxidase I. The stable pH range is 5.3 to 7.5. The pH range is determined by treating the enzyme at 50° C. for 60 minutes at each pH (phosphate buffer, Tris-HCl buffer, sodium acetate buffer) and then assaying the residual activity. The results are shown in FIG. 2.

III. Method for Determination of Titer

The amount of enzyme which catalyzes the reaction of decomposing 1 μmole of cholesterol at 37° C. for one minute in the presence of oxygen is defined as one unit. The titer is determined as follows. While shaking, the enzyme acts on cholesterol and 4-aminoantipyrine and phenol are reacted with the formed hydrogen peroxide in the presence of peroxidase to form quinonimine pigment. Absorption of the thus formed quinonimine pigment in the visible region is measured to determine the amount of hydrogen peroxide generated. Thus, the titer of the enzyme is determined. Hereafter specific activity is defined as activity per 1 mg of protein (unit/mg) Furthermore, an amount of enzyme protein is determined by absorbance at 280 nm (1 mg/ml when absorbance is 1).

a) Principle

The enzyme activity is determined by reacting hydrogen peroxide generated by the enzyme with 4-aminoantipyrine and phenol in the presence of peroxidase and quantitatively determining the formed quinonimine pigment. The reaction is shown by the following equations (1) and (2).

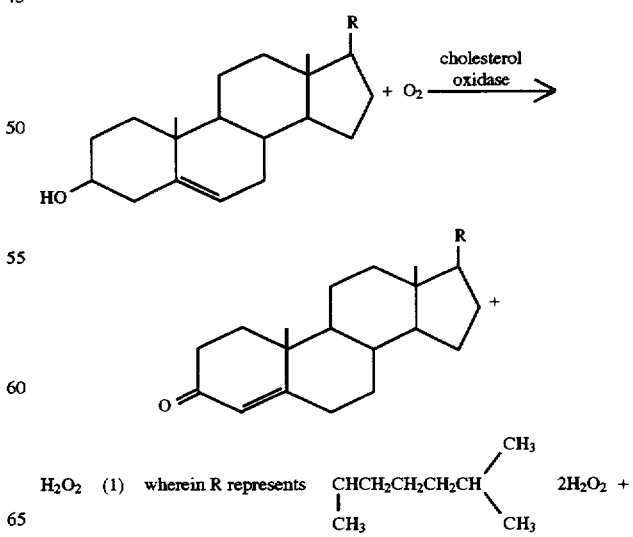

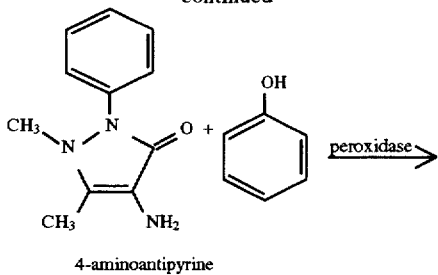

4-aminoantipyrine

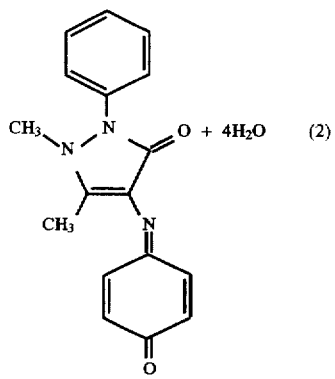

(b) Procedure

In a test tube, there are charged 1.0 ml of 3 mM cholesterol solution (which is prepared by adding 6 ml of 50 mM cholesterol ethanol solution to 94 ml of 1.05% Triton X-100 solution with stirring, heating the mixture for 10 minutes on a water bath, cooling the mixture in water, adding distilled water to the mixture until the total volume is 100 ml; and is not allowed to be used 30 minutes or longer after preparation), 0.3 ml of 50 mM sodium bilate solution, 0.3 ml of 0.5 mM potassium-sodium phosphate buffer (pH 6.6), 0.5 ml of 42 mM phenol, 0.5 ml of 2.4 mM 4-aminoantipyrine and 0.2 ml of 115 units/ml horseradish-derived peroxidase. The mixture is agitated. After maintaining at 37° C. for 3 minutes, 0.2 ml of an enzyme solution is added to the mixture. While shaking, the reaction is carried out at 37° C. for 5 to 10 minutes. Then, absorbance is measured at 500 nm (OD 500 nm)

(c) Calculation of Titer

One unit of cholesterol oxidase II corresponds to an enzyme activity which decomposes 1 μmole of cholesterol at 37° C. for 1 minute. On the other hand, it is reported that absorption coefficient of 1 mM quinonimine is 5.33 [Clinical Chemistry, 20, 470 (1974)]. Therefore, titer (A) per 1 ml of enzyme solution to be determined is calculated according to equation (2), by defining OD 500 nm for 3 ml of the reaction solution as described in (1) below.

(1) A difference obtained by subtracting [(OD 500 nm of reagent blank)−(OD 500 nm of the solution from which substrate has been removed from the reagent blank)] from [(OD 500 nm of the reaction solution containing both enzyme and substrate)−(OD 500 nm of the reaction solution from which substrate has been removed from the reaction solution)] is defined to be ΔE.

(2) Titer of enzyme solution A (unit/ml)=ΔE 5.33 time (min)×3×dilution rate

Note 1: Reagent blank means a solution obtained by removing enzyme solution from the reaction solution.

IV. Optimum Temperature

Figure 3:
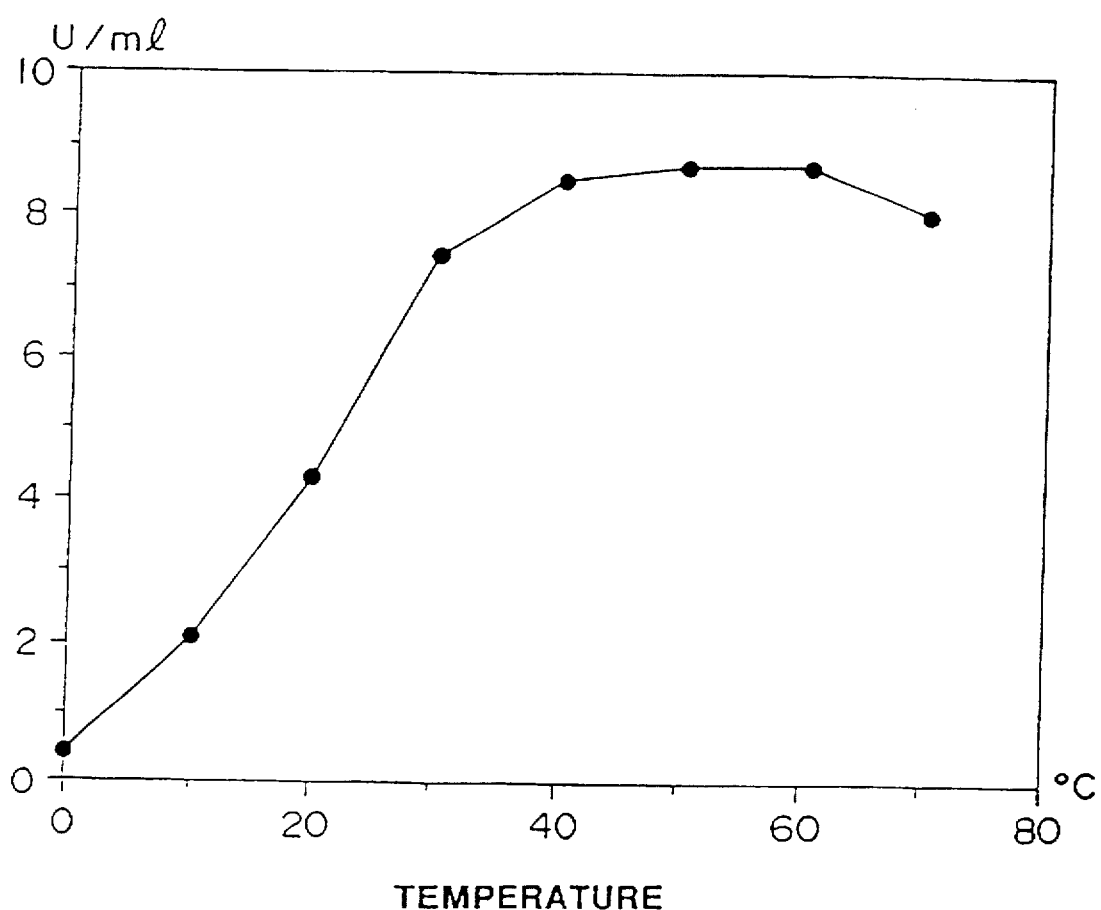
FIG. 3 shows the working temperature of the purified preparation of cholesterol oxidase II.

The optimum temperature at a pH of 6.6 for 3 minutes of the reaction time was examined. The results are shown in FIG. 3. The optimum temperature is at about 50° C.

V. Inactivation by pH and Temperature

Figure 4:
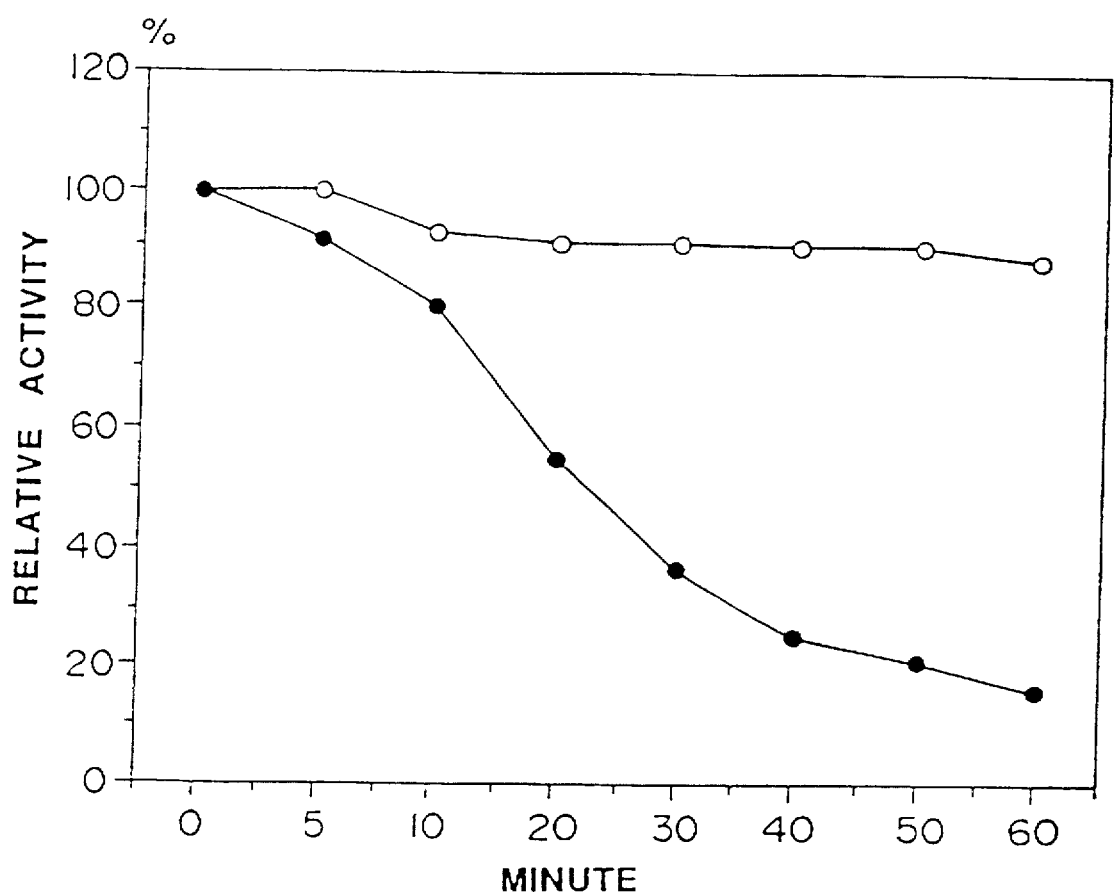
FIG. 4 shows thermostability of the purified cholesterol oxidase II. In the figure, ○ denotes the thermostabilty at 50° C. and ● denotes the thermostability at 60° C.

Cholesterol oxidase II is inactivated at pH of 8.5 or more. After heat treatment at pH of 7.0 for 60 minutes in 0.05M phosphate buffer, the residual activity was determined. As shown in FIG. 4, the results reveal that the enzyme is inactivated by about 10% at 50° C. and by about 83% at 60° C.

VI. Substrate Affinity

Michaelis' constant (Km value) of cholesterol oxidase II to cholesterol substrate was $3.0 \times 10^{-5}$M, whereas that of cholesterol oxidase I was $1.1 \times 10^{-3}$M. Reaction rates of the two enzymes were measured in various concentrations of cholesterol. The results are shown in FIG. 5. Km value of cholesterol oxidase II was about the one-hundredth of that of cholesterol oxidase I. It is indicated that affinity of cholesterol oxidase II to cholesterol is extremely high and more suited for quantitative determination of cholesterol. In addition, as is illustrated in FIG. 5, the saturation curve obtained by use of cholesterol oxidase II is a type of so-called Michaelis-Menten. The substrate activation phenomenon was not observed, while it was observed with cholesterol oxidase I. It is concluded that cholesterol oxidase II has superior reactivity to cholesterol oxidase I in quantitative determination of serum cholesterol at a low concentration.

Michaelis' constant was determined from the Lineweaver-Burk plot [refer to J. Am. Chem. Soc., 56, 658 (1934)].

VII. Determination of the Amino Acid Sequence and Nucleotide Sequence of Cholesterol Oxidase II The nucleotide sequence of cholesterol oxidase II is determined by the method of Sanger [refer to F. Sanger, Science, 214, 1205 (1981)] using Sequenase Ver 2.0 [trademark, manufactured by United States Biochemical].

Hereafter the present invention is described in more detail, with reference to the examples.

Example 1

Cloning of Cholesterol Oxidase II-encoding Gene

1) Preparation of Chromosomal DNA Containing Cholesterol Oxidase II-encoding Gene Brevibacterium sterolicum ATCC 21387 strain was cultured with shaking at 30° C. for 3 days in 30 ml of an LB medium [10 g/l Bactotrypton, 8 g/l Bacto-yeast extract (both were manufactured by Difco Co.), 5 g/l NaCl (pH 7.2)]. The resulting cells were collected by centrifugation at 4° C. for 10 minutes at 10,000 rpm using a cooling centrifuging machine (RPR20-2 rotor) manufactured by Hitachi Ltd. After washing the cells with 10.3% sucrose solution, the solution was again centrifuged to collect the cells. The whole chromosomal DNA was extracted by the method described in Current Topics in Microbiology and Immunology, 96 (1982) to give about 1 mg of chromosomal DNA.

2) Incorporation of Chromosomal DNA Fragment into Vector DNA

72 μg of the whole chromosomal DNA obtained in 1) above was taken and dissolved in 1,000 μl of M buffer [10 mM Tris-HCl buffer (pH 7.5), 10 mM $MgCl_2$, 50 mM NaCl, 1 mM DTT (dithiothreitol)]. 3.6 units of restriction endonuclease Sau3AI (manufactured by Takara Shuzo Co., Ltd.) was added to the solution to effect restriction digestion at 37° C. for 30 minutes. Then, the fractionation was carried out by 10 to 40% sucrose density gradient centrifugation according to the method described in Molecular Cloning supra. Centrifugation was performed at 20° C. for 16 hours at 26,000 rpm using an ultracentrifuging machine (SRP 28 rotor)

manufactured by Hitachi Ltd. The fractionation was carried out again and an part of each fraction was subjected to agarose gel electrophoresis according to the method described in Molecular Cloning supra to determine the size of DNA fragments. The fractions containing the DNA fragments of 3 to 6 kb were collected followed by ethanol precipitation. Thereafter, the precipitates were dissolved in 60 μl of a ligation buffer |66 mM Tris-HCl buffer (PH 7.6), 5 mM MgCl₂, 5 mM DTT, 1 mM ATP| to give the chromosomal DNA solution containing about 5 μg of the DNA fragment. Furthermore, 10 μg of pPROK-C (manufactured by Clone Tech Co., Ltd.) used as a vector was dissolved in 300 μl of M buffer and 40 units of restriction endonuclease BamHI (manufactured by Takara Shuzo Co., Ltd.) was added to the solution. The reaction was carried out at 37° C. for 3 hours to fully digest the vector. Then, 20 μl of 1M Tris-HCl buffer (pH 8.6) and 4 units of calf small intestine-derived alkaline phosphatase were added. The reaction was carried out at 37° C. for an hour for dephosphorylation. Further, by heating at 65° C. for 10 minutes, the enzyme was inactivated. After ethanol precipitation, the precipitates were dissolved in 80 μl of ligation buffer solution. Subsequently, 32 μl of a solution of chromosomal DNA digested with Sau3AI was mixed with 5 μl of a solution of pPROK-C digested with BamHI. The ligation buffer was added until the whole volume was 75 μl, and 2 units of T4 DNA ligase (manufactured by Takara Shuzo Co., Ltd.) was added to the mixture. Ligation was performed at 16° C. for 16 hours to give various recombinant DNA mixtures.

3) Transformation of *Escherichia coli*

With the recombinant DNA mixtures obtained in 2) above, *Escherichia coli* was transformed. The DNA-sensitive strain used for transformation was prepared by the method of Hanahan et al. described in Journal of Molecular Biology, 166, 577. *Escherichia coli* MM294 strain was cultured in LB medium overnight and 0.2 ml of the obtained culture was inoculated on 20 ml of SOB medium [20 g/l Bactotrypton, 0.50 g/l Bacto-yeast extract (both were manufactured by Difco Co.), 10 mM NaCl, 2.5 mM KCl, 10 mM MgCl₂, 10 mM MgSO₄ (pH 7.0)]. After culturing for 3 hours, the culture was transferred to a test tube of Falcon 2070 and settled in ice for 15 minutes. By centrifugation at 4° C., the cells were collected. The cells were suspended in 7 ml of TFB [10 mM Good MES buffer (pH 6.20), 100 mM RbCl, 45 mM MnCl₂, 10 mM CaCl₂, 3 mM hexamine cobalt chloride] and the suspension was settled in ice for 15 minutes. The cells were collected by centrifugation and again suspended in 1.6 ml of TFB. Then, 56 μl of dimethylsulfoxide was added to the resulting suspension. After gently stirring in ice for 5 minutes, 56 μl of β-mercaptoethanol was added and the mixture was gently stirred in ice for 10 minutes. Again 56 μl of dimethylsulfoxide was added and the mixture was gently stirred in ice for 5 minutes. The thus obtained cells were used for transformation as the DNA-sensitive strain. After 210 μl of the resulting solution containing DNA-sensitive strains was charged in Falcon 2059 test tube, 10 μl of the recombinant DNA mixtures prepared in 2) was added thereto. After gently stirring, the mixture was settled in ice for 30 minutes. The mixture was heated for 90 seconds in a thermostat of 42° C., then transferred into ice, and kept for 2 minutes. To the mixture was added 800 μl of SOC medium (SOB medium supplemented with 20 mM glucose). The resulting culture was inoculated on LB solid medium containing 0.1% cholesterol, 0.1% Triton X-100 and 0.0025%-ampicillin followed by culturing at 37° C. overnight. The colonies grown were obtained as transformants.

Figure 6:
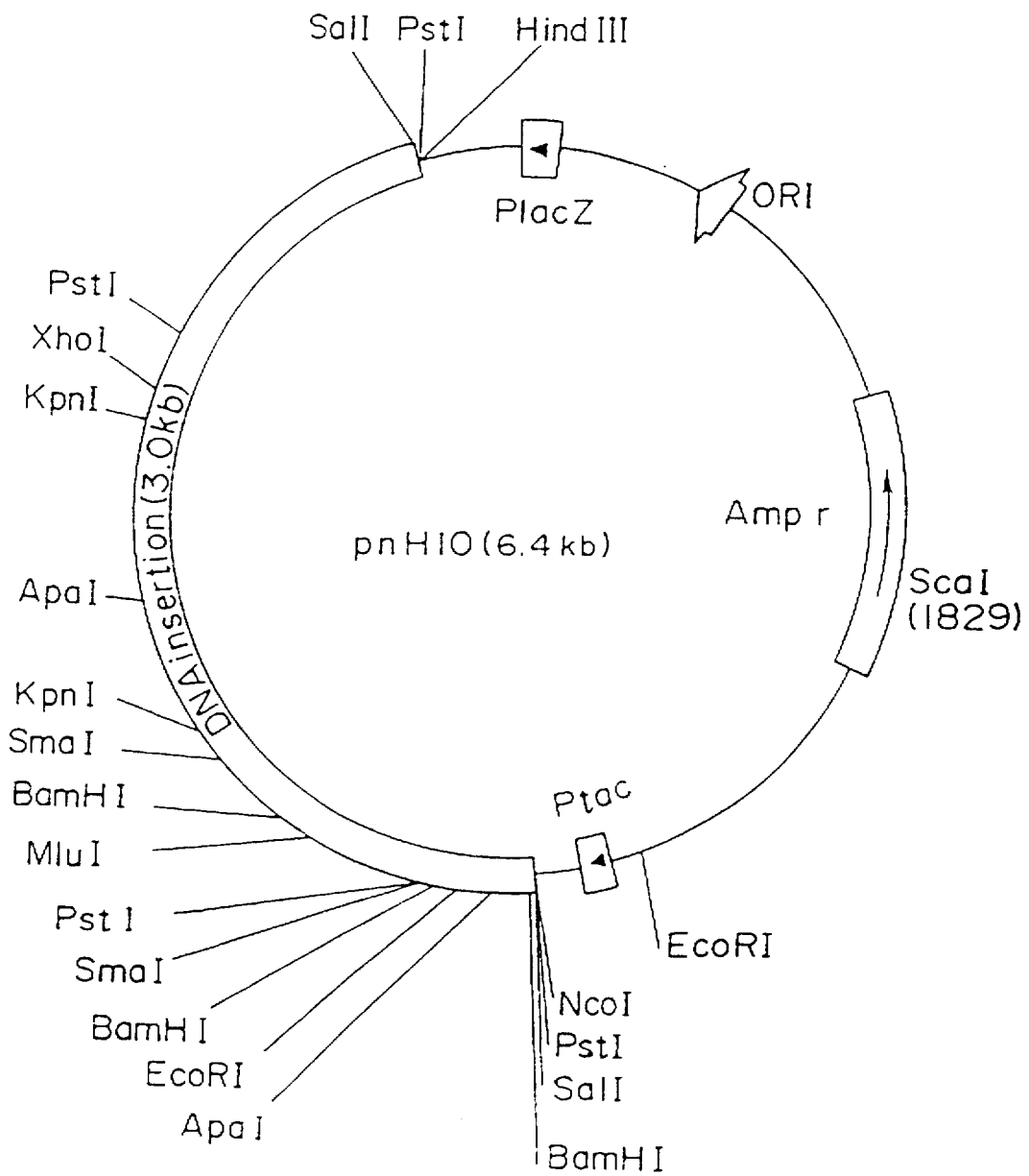
FIG. 6 shows the cleavage map for restriction enzymes of recombinant plasmid pnH10.

4) Selection of Transformants Carrying the Recombinant DNA Containing Cholesterol Oxidase II Encoding Gene The recombinant DNA containing cholesterol oxidase II-encoding gene was isolated from the transformants obtained in 3) described above by the following method. The colonies which grew on the LB solid medium and around which a clear halo formation was formed were selected. The colonies were inoculated on a microtiter plate to assay the presence or absence of cholesterol oxidase activity. The transformants having the cholesterol oxidase activity were inoculated on LB medium containing 0.005% of ampicillin followed by culturing at 30° C. overnight. After completion of the culturing, the cells were collected. The obtained cells were suspended in 10 ml of 0.05M phosphate buffer (pH 7.0) and then disrupted for 10 minutes by ultrasonic cell disrupter (Cell Disrupter, Model 200, manufactured by Branson Co., output: 40%). After centrifugation, cholesterol oxidase activity of the resulting supernatant was determined by the method described above. Thus, *Escherichia coli* nH10 having a high cholesterol oxidase activity was obtained. From the transformant nH10, a recombinant plasmid DNA carried by the transformant was recoverd to give pnH10. pnH10 was cleaved with HindIII, PstI, SalI, XhoI, KpnI, ApaII, BamHI, MluI, EcoRI, SmaI and ScaI and the structure of pnH10 was recognized by agarose gel electrophoresis. pnH10 had such a structure that DNA fragment of about 3.0 kb had been incorporated into pPROK-C (cf. FIG. 6).

5) Analysis of Cloned Cholesterol Oxidase II-encoding Gene

It was ascertained by the following method that pnH10 was a recombinant plasmid containing a gene coding for isoenzyme different from known cholesterol oxidase I produced by *Brevibacterium sterolicum* ATCC 21387. That is, recombinant plasmid pnH10 was prepared from nH10 strain according to the method described in Molecular Cloning (T. Maniatis, E. F. Fritsch, J. Sambrook, Cold Spring Harbour Publishing Co., 1982). After agarose gel electrophoresis, the gel containing pnH10 was dipped in a solution containing 1.5M NaCl and 0.5 M NaOH at room temperature for 30 minutes to denature double stranded DNA. By closely contacting the gel with a nylon filter, a solution containing 1.5M NaCl and 0.25M NaOH was permeated through the back surface of the filter, whereby the denatured DNA was transferred and fixed on the filter. The thus prepared filter was reacted at 45° C. for 16 hours with hybridization buffer (53.0 g/l NaCl, 26.5 g/l sodium succinate, 10 mM EDTA, 5-fold Denhardt solution, 0.5% SDS, 0.1 mg/ml thermally denatured bovine thymus-derived DNA, pH 7.0) containing DNA probe obtained by labeling synthetic single DNA having DNA nucleotide sequence deduced from the partial amino acid sequence of cholesterol oxidase I produced by *Brevibacterium sterolicum* ATCC 21387, namely, Probe No. 1 as defined in the Sequence Listing by SEQ ID No. 2 and illustrated below:

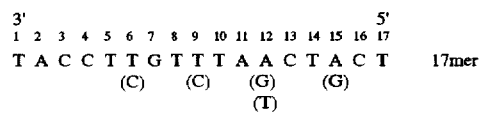

(wherein the 6th base is any one of T and C; the 9th base is any one of T and C; the 12th base is any one of A, G and T; the 15th base is any one of A and G; which becomes a mixture of 24 synthetic DNAs in combination); or Probe No. 2 as defined in the Sequence Listing by SEQ ID No. 3 and illustrated below:

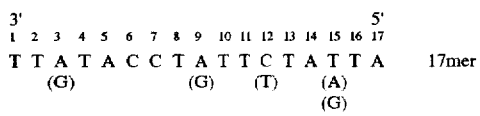

(wherein the 3rd base is any one of A and G; the 9th base is any one of A and G; the 12th base is any one of C and T; the 15th base is any one of T, A and G; which becomes a mixture of 24 synthetic DNAs in combination); with γ-$^{32}$P-ATP. Then, the solution containing the probe was discarded and the reaction mixture was thoroughly washed with 3-fold SSC at 65° C. The filter was closely contacted with X ray film, which was exposed at −70° C. for one day. By so-called autoradiography, the reactivity with pnH10 was examined. Probe No. 1 corresponds to the amino acid partial sequence of the polypeptide chain at the center of cholesterol oxidase I and probe No. 2 corresponds to the amino acid sequence at the C-terminal. The analyses of autoradiography indicate that pnH10 did not react with Probe Nos. 1 and No. 2, at all. The results reveal that the cholesterol oxidase II-encoding gene contained in plasmid pnH10 is different from the cholesterol oxidase I-encoding gene.

Example 2

Figure 7:
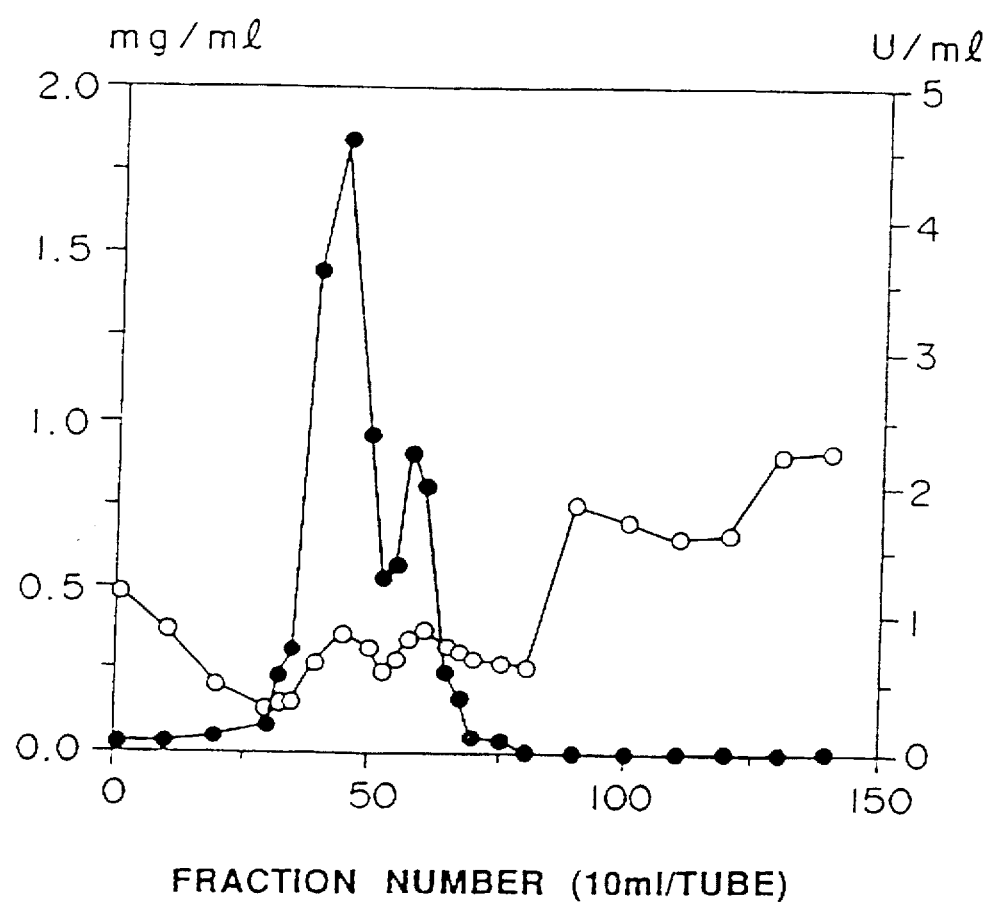
FIG. 7 shows elution pattern in ion exchange chromatography of cholesterol oxidase II using DEAE-Cellulofine. In the figure, ○ denotes protein concentration (OD 280 nm, mg/ml) of the eluate and ● denotes enzyme activity (U/ml) of the eluate.

*Escherichia coli* nH10 (FERM BP-2850) was inoculated on 3 ml of a seed medium (pH 7.2 prior to sterilization) obtained by supplementing 0.005% of ampicillin to LB medium and cultured with shaking at 30° C. for 18 hours. Three milliliters of the seed culture was put into each of five 2l-Erlenmeyer's flasks provided with baffles and containing 500 ml of the medium having the same components as the seed medium described above. Shaking culture was carried out at 30° C. for 16 hours. After culturing, the obtained culture was centrifuged at 10,000×g for 20 mintues with a cooling centrifuging machine to give about 18.6 g (wet cell weight) of the cells. To the obtained cells were added 186 ml of 0.01M phosphate buffer (pH 7.0, hereafter referred to as Buffer) to suspend the cells. Ultrasonication was performed for 30 minutes using an ultrasonication homogenizer (cell disrupter, Model 200, manufactured by Branson Co.; output of 75%, pulse retention time of 70%, mounted with a flat chip). After sonication, the disrupted mixture was centrifuged at 20,000×g for 15 minutes with a cooling centrifuging machine and the supernatant was obtained as the cell-free extract. Solid ammonium sulfate was added to 194 ml of the obtained cell-free extract to 60% saturation. While keeping pH at 7 with 1N NaOH solution, the mixture was gently stirred. After ammonium sulfate was completely dissolved, stirring was continued for further 30 minutes. Then, the solution was centrifuged at 20,000×g for 15 minutes with a cooling centrifuging machine to give the supernatant. The obtained supernatant was dialyzed to a cellophane tube as a dialysis membrane for 12 hours per liter of Buffer. Thereafter Buffer was exchanged and dialysis was performed for further 12 hours to effect desalting. After the dialysis, 98.5 ml of the crude enzyme solution was passed through a column (φ7.5×15 cm) of DEAE-Cellulofine (manufactured by Biochimical Industry Co., Ltd.), which had been previously equilibrated with Buffer. By washing with 3 liters of Buffer at a flow rate of 480 ml/hr, unadsorbed protein was washed out. Next, NaCl concentration was changed linearly from 0 to 0.5M to elute the enzyme with density gradient. Among the eluted fractions, the fraction having a specific activity of 10 units/mg or more was collected. Elution pattern is shown in FIG. 7.

Figure 8:
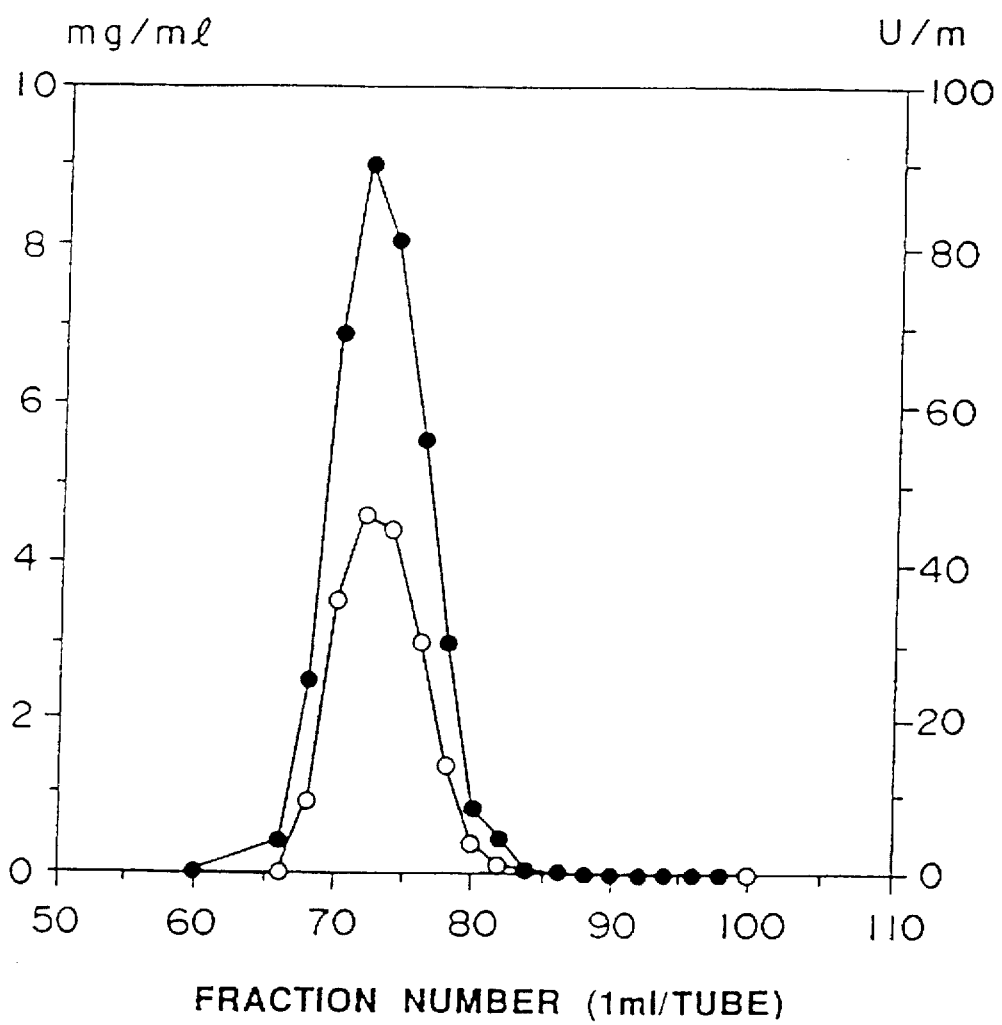
FIG. 8 shows elution pattern in gel filtration of cholesterol oxidase II using Superose prep12 HR16/50. In the figure, ○ denotes protein concentration (OD 280 nm, mg/ml) of the eluate and ● denotes enzyme activity (U/ml) of the eluate.

The obtained active fraction was concentrated by adding ammonium sulfate to 60% saturation. The formed precipitates were dissolved in Buffer and the solution was dialyzed as described above to effect desalting. The solution was further concentrated to about 2 ml by ultrafiltration. The concentrate was passed through a column (φ1.3×50 cm) of Superose prep12 HR16/50 (manufactured by Pharmacia Fine Chemicals Co., Ltd.), which had been previously equilibrated with 0.05M phosphate buffer (pH 7.0) supplemented with 0.3M NaCl and connected with 880PU pump (manufactured by Nippon Bunko) to perform elution at a flow rate of 30 ml/hr. Among the eluted fractions, the fractions having a specific activity of 15 units/mg or more were collected and dialyzed against 1 liter of Buffer. Elution pattern is shown in FIG. 8. The obtained active fraction was passed through a column (φ3.2×4.0 cm) of hydroxyappatite (manufactured by Biochemical Industry Co., Ltd.), which had been previously equilibrated with Buffer. By washing in Buffer at a flow rate of 100 ml/hr, the activity was all recovered in the washing liquid. The washing liquid was concentrated by ultrafiltration and the concentrate was made the purified enzyme preparation. The foregoing steps for purification are summarized in Table 4.

TABLE 4

| Step | Total Activity (U) | Total Protein (mg) | Specific Activity (U/mg) | Yield (%) |
|---|---|---|---|---|
| Cell-free extract | 1462 | 6940 | 0.21 | 100 |
| Fraction with ammonium sulfate (0–60%) | 2368 | 5990 | 0.40 | 162 |
| DEAE-Cellulofine | 844 | 57 | 14.8 | 57.7 |
| Superose prep12 | 740 | 39 | 19.1 | 51.0 |
| Hydroxyappatite | 404 | 20 | 20.4 | 28.0 |

Further in order to assay the purity of the purified enzyme preparation, the sample in the non-denatured state as obtained above was applied to polyacrylamide gel electrophoresis. The assay was carried out according to the method of Davis et al. [B. J. Davis et al., Annals of New York Academy of Science, 121, 404 (1964)]. The results reveal that the purified enzyme preparation was homogeneous.

What is claimed is:

1. An isolated cholesterol oxidase which is derived from *Brevibacterium sterolicum* and has the following physicochemical properties:

(a) activity which catalyzes the reaction of oxidizing cholesterol in the presence of oxygen to form hydrogen peroxide and 4-cholesten-3-one;

(b) an isoelectric point at a pH of 4.7;

(c) substrate specificity so that the enzyme acts on cholesterol, β-sitosterol, stigmasterol, pregnenolone, dehydroisoandrosterone and estradiol but does not act on vitamin $D_3$, cholic acid, androsterone, cholesterol linoleate or lanosterol;

(d) a working pH in a range of 5.0 to 7.5, and the enzyme is stabile in a pH range of 5.3 to 7.5 when heated at 50° C. for 60 minutes;

(e) optimum temperature of about 50° C.;

(f) the enzyme is inactivated at a pH of 10.0 or more or at a pH of 4.0 or less when heated at 50° C. for an hour and the enzyme is also inactivated by about 83% when heated at a pH of 7.0 and a temperature of 60° C. for an hour;

(g) the enzyme is inhibited by p-chloromercury benzenesulfonate, silver nitrate and o-hydroxyquinoline and in the presence of bovine serum albumin, resistance to heat and stability during storage are improved;

(h) molecular weight of about 43,000 (gel filtration); and (i) $3.0 \times 10^{-5}$ M of Michaelis' constant to cholesterol, when Michaelis' constant is determined in a 0.5 mM potassium sodium phosphate buffer (pH 6.6) at 37° C. for 10 minutes.

2. An isolated cholesterol oxidase according to claim 1, wherein said *Brevibacterium sterolicum* is deposited with the American Type Culture Collection as ATCC 21387.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 1545 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i v ) ORIGINAL SOURCE:
    ( A ) ORGANISM: Brevibacterium sterolicum
    ( B ) STRAIN: ATCC 21387
    ( G ) CELL TYPE: Unicellular organism ( v i i i ) IMMEDIATE SOURCE:
    ( A ) LIBRARY: genomic
    ( B ) CLONE: pnH10

( x i ) SEQUENCE DESCRIPTION: SEQ ID NO:1:

| | | | | | | |
|---|---|---|---|---|---|---|
| ATGACGGTCA | ACGACGAGCA | GTTACGGCTG | TCCCGGCGAG | GATTCCTCAC | CGCGGGCGCT | 60 |
| GCGGGCGCCG | GCGTGCTGGC | AGCCGGCGCA | CTCGGCGGCT | GGACCCCGGC | CTTCGCCGTC | 120 |
| CCTGCCGGTT | CCGCCGGCTC | CCTCGGATCG | CTCGGATCGA | CCGGGCCGGT | CGCGCCGCTT | 180 |
| CCGACGCCGC | CGAACTTCCC | GAACGACATC | GCGCTGTTCC | AGCAGGCGTA | CCAGAACTGG | 240 |
| TCCAAGGAGA | TCATGCTGGA | CGCCACTTGG | GTCTGCTCGC | CAAGACGCC | GCAGGATGTC | 300 |
| GTTCGCCTTG | CCAACTGGGC | GCACGAGCAC | GACTACAAGA | TCCGCCCGCG | CGGCGCGATG | 360 |
| CACGGCTGGA | CCCCGCTCAC | CGTGGAGAAG | GGGGCCAACG | TCGAGAAGGT | GATCCTCGCC | 420 |
| GACACGATGA | CGCATCTGAA | CGGCATCACG | GTGAACACGG | GCGGCCCCGT | GGCTACCGTC | 480 |
| ACGGCCGGTG | CCGGCGCCAG | CATCGAGGCG | ATCGTCACCG | AACTGCAGAA | GCACGACCTC | 540 |
| GGCTGGGCCA | ACCTGCCCGC | TCCGGGTGTG | CTGTCGATCG | GTGGCGCCCT | TGCGGTCAAC | 600 |
| GCGCACGGTG | CGGCGCTGCC | GGCCGTCGGC | CAGACCACGC | TGCCCGGTCA | CACCTACGGT | 660 |
| TCGCTGAGCA | ACCTGGTCAC | CGAGCTGACC | GCGGTCGTCT | GGAACGGCAA | CACCTACGCA | 720 |
| CTCGAGACGT | ACCAGCGCAA | CGATCCTCGG | ATCACCCAC | TGCTCACCAA | CCTCGGGCGC | 780 |
| TGCTTCCTGA | CCTCGGTGAC | GATGCAGGCC | GGCCCAACT | TCCGTCAGCG | GTGCCAGAGC | 840 |
| TACACCGACA | TCCCGTGGCG | GGAACTGTTC | GCGCCGAAGG | GCGCCGACGG | CCGCACGTTC | 900 |
| GAGAAGTTCG | TCGCGGAATC | GGGCGGCGCC | GAGGCGATCT | GGTACCCGTT | CACCGAGAAG | 960 |
| CCGTGGATGA | AGGTGTGGAC | GGTCTCGCCG | ACCAAGCCGG | ACTCGTCGAA | CGAGGTCGGA | 1020 |
| AGCCTCGGCT | CGGCGGGCTC | CCTCGTCGGC | AAGCCTCCGC | AGGCGCGTGA | GGTCTCCGGC | 1080 |
| CCGTACAACT | ACATCTTCTC | CGACAACCTG | CCGGAGCCCA | TCACCGACAT | GATCGGCGCC | 1140 |
| ATCAACGCCG | GAAACCCCGG | AATCGCACCG | CTGTTCGGCC | CGGCGATGTA | CGAGATCACC | 1200 |
| AAGCTCGGGC | TGGCCGCGAC | GAATGCCAAC | GACATCTGGG | GCTGGTCGAA | GGACGTCCAG | 1260 |
| TTCTACATCA | AGGCCACGAC | GTTGCGACTC | ACCGAGGGCG | GCGGCGCCGT | CGTCACGAGC | 1320 |
| CGCGCCAACA | TCGCGACCGT | GATCAACGAC | TTCACCGAGT | GGTTCCACGA | GCGCATCGAG | 1380 |
| TTCTACCGCG | CGAAGGGCGA | GTTCCCGCTC | AACGGTCCGG | TCGAGATCGC | TGCTGCGGGC | 1440 |
| TCGATCAGGC | AGCCGACGTC | AAGGTGCCGT | CGGTGGGCCC | GCCGACCATC | TCGGCGACCC | 1500 |
| GTCCGCGTCC | GGATCATCCG | GACTGGGACG | TCGCGATCTG | GCTGA | | 1545 |

( 2 ) INFORMATION FOR SEQ ID NO:2:

( i ) SEQUENCE CHARACTERISTICS:
        ( A ) LENGTH: 17 base pairs (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: YES (x) PUBLICATION INFORMATION:
          (A) AUTHORS: Fujishiro, Kinya
                       Ohta, Toshio
                       Hasegawa, Mamoru
                       Yamaguchi, Kazuo
                       Mizukami, Toru
                       Uwajima, Takayuki
          (B) TITLE: ISOLATION AND IDENTIFICATION OF THE GENE OF
               CHOLESTEROL OXIDASE FROM BREVIBACTERIUM STEROLICUM
               ATCC 21387, A WIDELY USED ENZYME IN CLINICAL
               ANALYSIS
          (C) JOURNAL: Biochem. Biophys. Res. Commun.
          (D) VOLUME: 172
          (E) ISSUE: 2
          (F) PAGES: 721-727
          (G) DATE: 30-OCT-1990

(x) PUBLICATION INFORMATION:
          (A) AUTHORS: Fujishiro, Kinya
                       Ohta, Toshio
                       Hasegawa, Mamoru
                       Mizukami, Toru
                       Uwajima, Takayuki
          (B) TITLE: ISOLATION AND IDENTIFICATION OF THE GENE OF
               CHOLESTEROL OXIDASE FROM BREVI BACTERIUM STELORICUM
               ATCC 21387, A WIDELY USED ENZYME IN CLINICAL
               ANALYSIS
          (C) JOURNAL: Biochem. Biophys. Res. Commun.
          (D) VOLUME: 173
          (E) ISSUE: 3
          (F) PAGES: 1383-1384
          (G) DATE: 30-OCT-1990

(xi) SEQUENCE DESCRIPTION: SEQ ID NO:2:

TCRTCDATYT GYTCCAT                                                            17

(2) INFORMATION FOR SEQ ID NO:3:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: NO (x) PUBLICATION INFORMATION:
          (A) AUTHORS: Fujishiro, Kinya
                       Ohta, Toshio
                       Hasegawa, Mamoru
                       Yamaguchi, Kazoo
                       Mizukami, Toru
                       Uwajima, Takayuki
          (B) TITLE: ISOLATION AND IDENTIFICATION OF THE GENE OF
               CHOLESTEROL OXIDASE FROM BREVIBACTERIUM STEROLICUM
               ATCC 21387, A WIDELY USED ENZYME IN CLINICAL
               ANALYSIS
          (C) JOURNAL: Biochem. Biophys. Res. Commun.
          (D) VOLUME: 172
          (E) ISSUE: 2
          (F) PAGES: 721-727
          (G) DATE: 30-OCT-1990

(x) PUBLICATION INFORMATION:

(A) AUTHORS: Fujishiro, Kinya
            Ohta, Toshio
            Hasegawa, Mamoru
            Yamaguchi, Kazuo
            Mizukami, Toru
            Uwajima, Takayuki
(B) TITLE: ISOLATION AND IDENTIFICATION OF THE GENE OF
           CHOLESTEROL OXIDASE FROM BREVIBACTERIUM STELORICUM
           ATCC 21387, A WIDELY USED ENZYME IN CLINICAL
           ANALYSIS
(C) JOURNAL: Biochem. Biophys. Res. Commun.
(D) VOLUME: 173
(E) ISSUE: 3
(F) PAGES: 13X3-1384
(G) DATE: 30-OCT-1990

(xi) SEQUENCE DESCRIPTION: SEQ ID NO:3:

ATDATYTTRT CCATRTT                           17